US00PP24454P3

(12) United States Plant Patent
Villegas

(10) Patent No.: US PP24,454 P3
(45) Date of Patent: May 13, 2014

(54) ***SANSEVIERIA* PLANT NAMED 'BLACK JACK'**

(50) Latin Name: *Sansevieria trifasciata*
Varietal Denomination: Black Jack

(75) Inventor: Marvin Gonzalez Villegas, San Ramon (CR)

(73) Assignee: Florica Farms, Inc., Eustis, FL (US)

( * ) Notice: Subject to any disclaimer, the term of this patent is extended or adjusted under 35 U.S.C. 154(b) by 0 days.

(21) Appl. No.: 13/374,904

(22) Filed: Jan. 23, 2012

(65) Prior Publication Data

US 2013/0191954 P1 Jul. 25, 2013

(51) Int. Cl.
*A01H 5/00* (2006.01)

(52) U.S. Cl.
USPC ..... Plt./382

(58) Field of Classification Search
USPC ..... Plt./382, 263.1, 226
See application file for complete search history.

*Primary Examiner* — Kent L Bell
(74) *Attorney, Agent, or Firm* — Foley & Lardner LLP

(57) ABSTRACT

The new variety 'Black Jack' is part of the "compact *sansevieria* varieties". The plant can reach up to 40 cm in length, with about 7-10 leaves per plant. The plant is shaped like an inverted pyramid, the arrangement of the leaves is in the form of a rosette. Shows colors very similar to its parent variety ('Black Gold Superba'), however it doesn't show variegated bands into the margins and the margins show a brilliant yellow-green color, and presents more leaves per rosette than the parental variety 'Black Gold Superba'.

3 Drawing Sheets

Latin name of the genus and species of the claimed plant: *Sansevieria trifasciata.*

Variety denomination: 'Black Jack'.

BACKGROUND OF THE INVENTION

The present invention relates to a new and distinct cultivar of *Sansevieria* plant, botanically known as *Sansevieria trifasciata*, of the family Ruscaceae, hereinafter referred to by the cultivar name 'Black Jack'.

*Sansevieria* is a monocotyledonous and succulent, flowering plant which can be produced in either hard-leafed or soft-leafed varieties for interior use as a house plant or outdoor ornamental plant.

The new *Sansevieria* 'Black Jack' was discovered and selected by Mr. Marvin Gonzalez Villegas, as a single flowering plant within a planting of 'Black Gold Superba' at Monterrey, San Carlos, Alajuela province, Costa Rica in 2004 . It originated as a naturally-occurring mutation of the *Sansevieria* variety 'Black Gold Superba' (unpatented).

Asexual reproduction of the new *Sansevieria* cultivar by vegetative cuttings was first performed in January 2005 in Monterrey, San Carlos, Alajuela, Costa Rica, and demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'Black Jack', which in combination distinguish this *Sansevieria* as a new and distinct cultivar:

1. Green colored foliage with brilliant yellow-green margins and non-uniform horizontal variegated yellow-green bands in the leaf blade.

2. Wide and lanceolate leaves (30 cm long) and supported in a rosette.
3. 35-40 cm plant height.
4. Erect Plant habit.
5. Needs little water and is moderately drought tolerant.

The new variety 'Black Jack' is considered a variety of *Sansevieria* in the group denominated as "compact *Sansevieria* plants". The new variety 'Black Jack' presents an average of 7-10 leaves per plant when it reaches its maturity (between 8-10 months). The variety has an erect growth habit and the entire plant can reach a height range between 35 and 40 cm. The leaves are narrow (6.5 cm average measured at the widest part of the mature leaf) and lanceolate, with a soft waxy texture and the blades are thin and slightly wavy. The plant has an inverted triangle shape.

This variety is moderately drought tolerant and adapts to conditions of light and shade (interior and exterior).

The leaf blade is green colored (RHS 141A), and also presents non-uniform horizontal variegated bands on both sides of some leaves, with yellow-green RHS 149D and RHS 149B coloration. In addition, the leaves have irregular margins on both sides with an average width of 1 cm. The margin coloration is brilliant yellow-green (RHS 154B) and does not have bands into the margins.

Plants of the new *Sansevieria* 'Black Jack' differ from plants of the parental cultivar, 'Black Gold Superba' (unpatented) in the characteristics described in Table 1. The variety 'Black Gold Superba' gave rise to the var. 'Black Jack'. The 'Black Gold Superba' variety is also considered to be part of the "compact Sansevieria group". 'Black Gold Superba' shows less vigor than 'Black Jack', has fewer leaves per plant (3-4), and an average width of 6.5 cm (measured in the middle of the mature leaf.) The growth habit is erect and presents wide leaves supported in a rosette. The entire plant can reach a size between 30-40 cm, and the plant has, as for 'Black Jack', an inverted triangle shape. The leaves are lanceolate with a soft, waxy texture. The younger leaves show a yellowish green vivid coloration (RHS 134A) in the interior of the leaf blade. This area shows also irregular streaks or yellowish-green bands (RHS 142D) and the margins in both sides of the leaf are variegated with irregular horizontal bands that alternate between light yellowish green (RHS 142D) broad bands and brilliant yellowish green (RHS 149A) thin bands. When the leaf is mature, the deep color inside turns yellowish green (RHS 141B), while margins alternate between vivid greenish yellow (RHS 2A) and light-yellowish green (RHS 2C) colors.

TABLE 1

Comparison with Parental Variety

| Characteristic | New Cultivar 'Black Jack' | Female Parent 'Black Gold Superba' (unpatented) |
|---|---|---|
| Plant Vigor | more vigorous (more leaves) | less vigorous (less leaves) |
| Color | Green colored foliage with yellow-green margins and non-uniform horizontal variegated bands (yellow-green bands ) | green leaves with yellow margins. |
| Shape | wide and lanceolate leaves on a rosette | wide and lanceolate leaves |
| Texture of leaves | smooth-textured leaves | smooth-textured leaves |

Of the many commercial cultivars known to the present inventor, the most similar in comparison to the new *Sansevieria* 'Black Jack' is the parent variety *Sansevieria* 'Black Gold Superba' (unpatented), in the characteristics described in Table 1.

BRIEF DESCRIPTION OF THE PHOTOGRAPHS

The accompanying photographs illustrate the overall appearance of the new *Sansevieria* cultivar 'Black Jack' showing the colors as true as is reasonably possible with colored reproductions of this type. Colors in the photographs may differ slightly from the color value cited in the detailed botanical description which accurately describe the color of 'Black Jack'

DETAILED BOTANICAL DESCRIPTION

Figure 1:
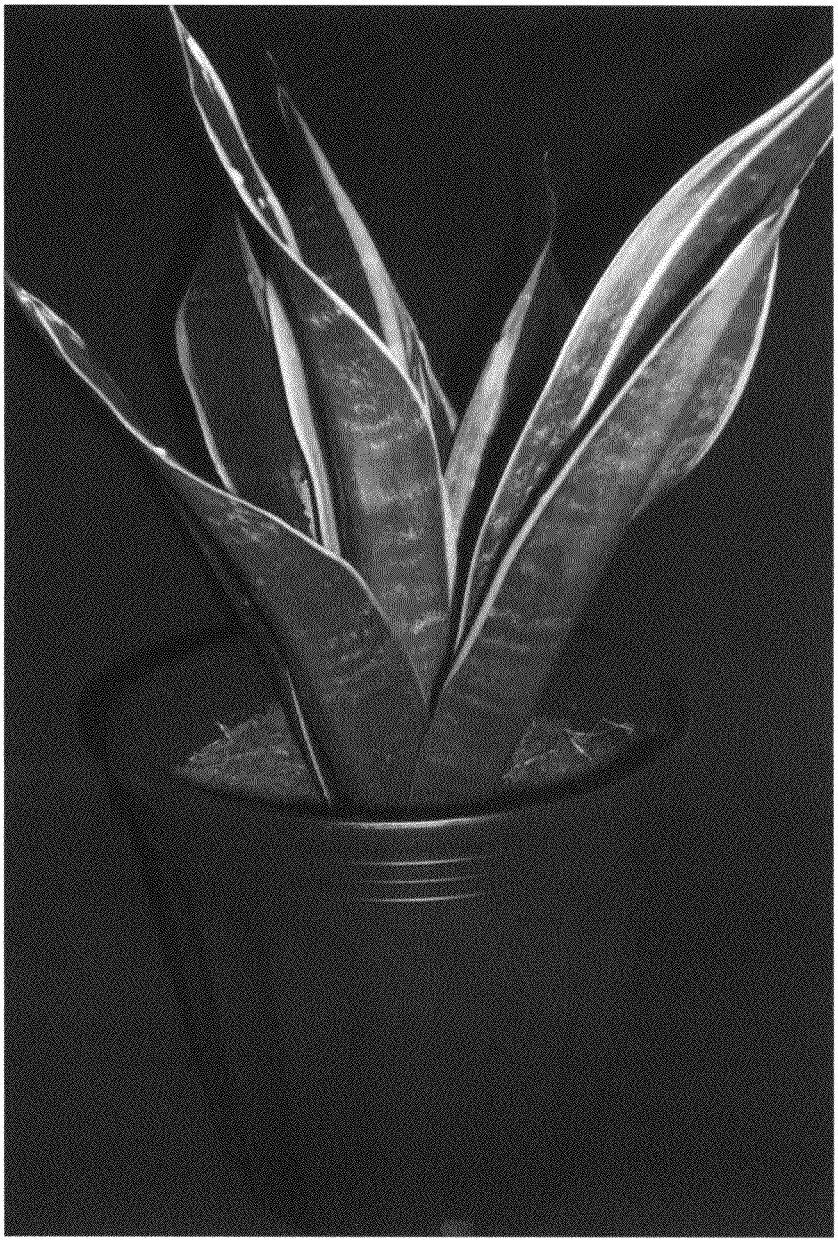
FIG. 1 Shows a side view of an eight-month old plant of *Sansevieria* 'Black Jack' in a 21 cm diameter pot.
Figure 2:
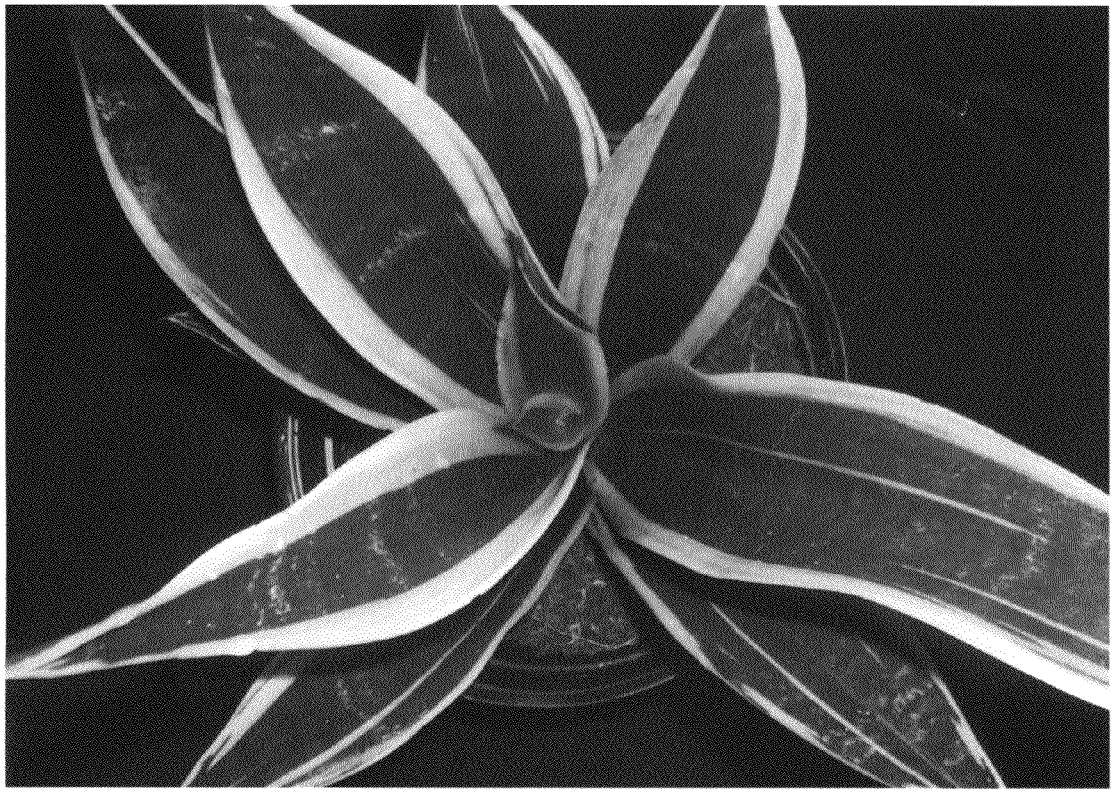
FIG. 2 Shows a top view of an eight-month old plant of *Sansevieria* 'Black Jack' in a 21 cm diameter pot.
Figure 3A:
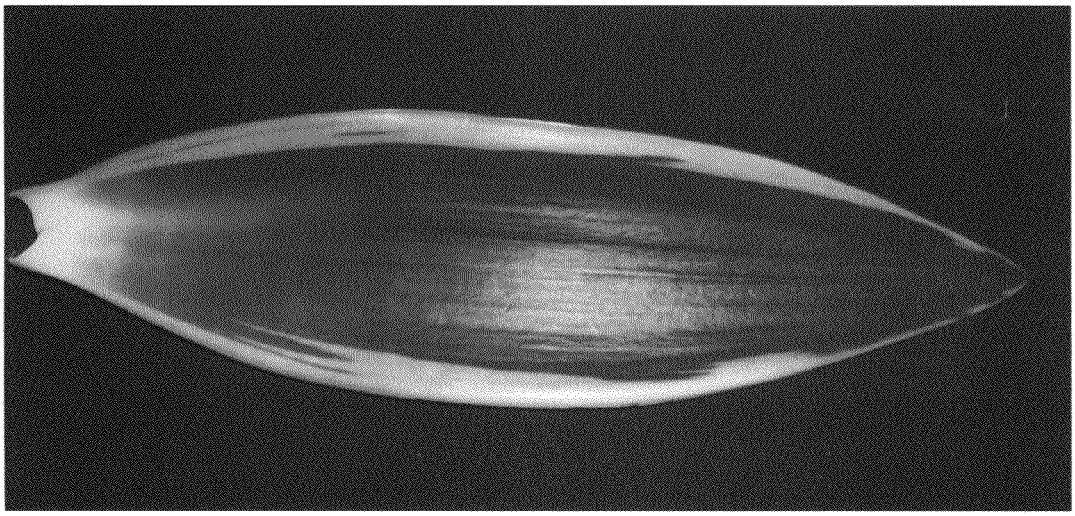
FIG. 3A Shows a close-up view of the upper side of a typical leaf of 'Black Jack' taken from an eight-month old plant.
Figure 3B:
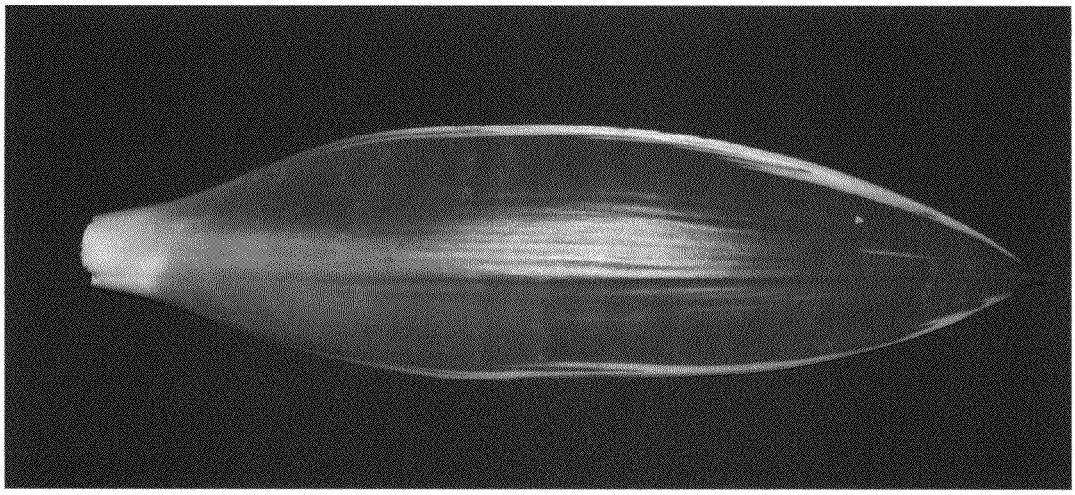
FIG. 3B Shows a close-up view of the lower side of a typical leaf of 'Black Jack' taken from an eight-month old plant.

The new *Sansevieria* 'Black Jack' has not been observed under all possible environmental conditions. The phenotype of the new cultivar may vary with variations in environment such as temperature, light intensity, and day length without any change on the genotype of the plant.

The aforementioned photographs, together with the following observations, measurements and values describe the new *Sansevieria* cultivar 'Black Jack' as grown in an open-field in Monterrey, San Carlos, Alajuela province, Costa Rica, which closely approximate those generally used in commercial practice. Average temperature at Monterrey is 24.5° C. during the day and 18° C. at night. Plants grow under natural light conditions.

This crop does not require constant fertilization, however, to increase production per area about 200 kg $ha^{-1}$ N, 150 kg $ha^{-1}$ of P and 100 kg $ha^{-1}$ K are required. Production is closely related with soil conditions in which the plants are grown.

Color references were made according to The Royal Horticultural Society Color Chart (R.H.S., April 2009). The photographs and descriptions were made during the rainy season in Monterrey, San Carlos, Alajuela province, Costa Rica, when outdoor day average temperature was 23° C. The age of the plants described is 8 months.

Classification:

*Botanical.*—*Sansevieria trifasciata.*

*Variety denomination.*—Black Jack.

Parentage: *Sansevieria trifasciata* 'Black Gold Superba' (unpatented).

Optimal growth conditions:

*Light intensities.*—High adaptability to outdoor or indoor conditions.

*Temperature.*—Day: 24° C. to 32° C. Night: 18° C. to 23° C.

*Temperature tolerance.*—Tolerant to temperatures between 12° C. and 35° C.

*Fertilization.*—200, 150 and 100 kg $ha^{-1}$ of N, P and K.

*Growth regulators.*—Not necessary.

Propagation:

*Type.*—Vegetative, by rooted cuttings.

*Rooting habit description.*—Rhizomes, with short roots.

*Time to initiate roots.*—15 to 22 days at 18-25° C.

*Time to produce a rooted cutting.*—About 60 to 90 days at 18-25° C.

Plant:

*General appearance and form.*—Height: Between 35 and 40 cm. Spread: Between 20 and 25 cm. Form: Monocot; leaf bases arranged in a rosette around growing point. Shape: inverted triangle.

*Growth rate and habit.*—About 2 cm per week; upright.

*Fragrance.*—None.

*Stem.*—Modified (Rhizome and foliage). Length: About 8 cm when grown in ground; About 6 cm when grown in 21 cm size container. Diameter: About 1.7 to 2 cm. Shape: round. Texture: rough. Color: RHS 17A. Strength: strong and durable. Internode length: About 0.3 mm to 0.7 mm.

Foliage:

*Quantity.*—About 7-10 leaves.

*Arrangement and attachment.*—Single, alternate; leaf bases arranged in a rosette around growing point.

*Leaf length.*—About 30 cm.

*Leaf width.*—About 6.5 cm.

*Overall shape of leaf.*—Lanceolate.

*Apex shape.*—Acute, triangular.

*Base shape.*—Plane.

*Margin.*—Sharp, smooth.

*Texture.*—Upper Surface: smooth and waxy texture. Under Surface: smooth and waxy texture.

*Pubescence.*—None.

*Color of mature leaf.*—Upper Surface: RHS 141A, with bands of RHS 149D and 149B and margins of 154A. Lower Surface: RHS 141A, with bands of RHS 149D and 149B and margins of 154A.

*Color of immature leaf.*—Upper Surface: RHS 141A, with bands of RHS 149D and 149B and margins of 154A. Lower Surface: RHS 141A, with bands of RHS 149D and 149B and margins of 154A.

*Venation.*—Pattern: longitudinal/parallel leaf shape. Color: None.

*Leaf fragrance.*—None.

Inflorescence description:

*Arrangement and type*.—Inflorescence.

*Orientation at opening*.—Out of the spike.

*Quantity per plant with at least one open flower*.—One inflorescence per plant. About 22 flowers opened 2 weeks after appearance of the spike. Flowers sporadically and profusely under growth conditions.

*Inflorescence size*.—Length: About 28 cm. Diameter: About 4 cm.

*Flower size*.—Length: About 2 cm. Diameter: About 1 cm. Depth: About 1 cm.

*Fragrance*.—Soft and pleasant.

*Bud*.—Rate of opening: About 7 to 8 days, according to weather. Shape: ovoid. Length: About 2 cm. Diameter: About 3.0 mm. Color: Apex: RHS 150A. Base: RHS 142A. Texture (both surfaces): smooth.

Petals:

*Quantity*.—6.

*Arrangement*.—Star-shaped. No further data on the instant plant's petals was collected.

Reproductive organs:

*Androecium*.—Stamen: Number: 5 per flower. Length: About 1.3 cm. Color: RHS 150C. Anther: Length: About 0.2 mm. Width : About 0.1 mm. Color: RHS 150C. Filament: Length: About 1.1 mm. Color: RHS 150C. Pollen: Amount: moderate. Color: RHS 154D.

*Gynoecium*.—Pistil: Number: One per flower. Length: About 2.1 cm. Stigma: Length: About 0.6 mm. Width: About 0.8 mm. Color: RHS 150C. Style: Length: About 1.3 mm. Color: RHS 150C. Ovary: Length: About 3 mm. Width: About 2.5 mm. Color: RHS 150C.

Fruits: None observed.

Weather resistance: Drought tolerant.

Disease/pest resistance: Not observed for disease/pest resistance.

Disease/pest susceptibility: Not observed for disease/pest susceptibility.

I claim:

1. A new and distinct variety of *Sansevieria* plant named 'Black Jack', substantially as illustrated and described herein.

* * * * *